(12) United States Patent (10) Patent No.: US 12,642,436 B2
Wang (45) Date of Patent: Jun. 2, 2026

(54) METHOD AND APPARATUS FOR MICROVASCULAR VESSEL IMAGING

(71) Applicants:MICROVASCULAR HEALTH SOLUTIONS, LLC, Alpine, UT (US); Omni Imaging, Inc., Philadelphia, PA (US)

(72) Inventor: Yongping Wang, Philadelphia, PA (US)

(73) Assignees: MICROVASCULAR HEALTH SOLUTIONS, LLC, Alpine, UT (US); Omni Imaging, Inc., Philadelphia, PA (US)

( * ) Notice: Subject to any disclaimer, the term of this patent is extended or adjusted under 35 U.S.C. 154(b) by 0 days.

(21) Appl. No.: 17/587,492

(22) Filed: Jan. 28, 2022

(65) Prior Publication Data

US 2022/0240785 A1 Aug. 4, 2022

Related U.S. Application Data

(60) Provisional application No. 63/222,032, filed on Jul. 15, 2021, provisional application No. 63/143,799, filed on Jan. 30, 2021.

(51) Int. Cl.
*A61B 5/00* (2006.01)
*A61B 5/02* (2006.01)
*A61B 5/026* (2006.01)

(52) U.S. Cl.
CPC .......... *A61B 5/0077* (2013.01); *A61B 5/0062* (2013.01); *A61B 5/0082* (2013.01); *A61B 5/02007* (2013.01); *A61B 5/0261* (2013.01)

(58) Field of Classification Search
CPC ........ A61B 2562/0233; A61B 5/02007; A61B 5/0077; A61B 5/0059; A61B 5/489; A61B 5/441; A61B 1/00188; G02B 21/006
See application file for complete search history.

(56) References Cited

U.S. PATENT DOCUMENTS 6,216,540 B1 4/2001 Nelson et al.
2007/0232874 A1* 10/2007 Ince ......................... A61B 5/72
600/320

(Continued)

FOREIGN PATENT DOCUMENTS

JP 2006-271843 A 10/2006
JP 4616681 B2 * 1/2011
WO 2018/168071 A1 9/2018

OTHER PUBLICATIONS

International Search Report and Written Opinion received for PCT Patent Application No. PCT/US2022/014411, mailed on Apr. 13, 2022, 15 pages.

*Primary Examiner* — Keith M Raymond
*Assistant Examiner* — Milton Truong
(74) *Attorney, Agent, or Firm* — Workman Nydegger

(57) ABSTRACT

Disclosed are methods and apparatuses for microvascular system imaging. In some embodiments, an apparatus for microvascular system imaging is a probe including at least one high-resolution image sensor module, at least one lens set, one or more optical filters, an illumination source, and a housing. In some embodiments, the lens set may be a miniature lens set. In some embodiments, the housing may be a tube structure. In some embodiments, the tube may be covered with a protective and/or sterile cover. The cover may be optically non-distorting. The imaging probe may additionally include a removable cap.

15 Claims, 10 Drawing Sheets

(56)          References Cited

U.S. PATENT DOCUMENTS

| | | | |
|---|---|---|---|
| 2008/0081950 A1* | 4/2008 | Koenig | G02B 23/2423 |
| | | | 600/178 |
| 2009/0009759 A1* | 1/2009 | Backman | G01J 3/0208 |
| | | | 356/303 |
| 2009/0048486 A1* | 2/2009 | Surti | A61B 1/0008 |
| | | | 600/127 |
| 2011/0137178 A1* | 6/2011 | Tearney | A61B 5/037 |
| | | | 600/476 |
| 2012/0232342 A1* | 9/2012 | Reydel | A61B 1/31 |
| | | | 600/116 |
| 2014/0022365 A1* | 1/2014 | Yoshino | A61B 1/07 |
| | | | 348/65 |
| 2015/0112132 A1* | 4/2015 | Nieman | A61B 1/00142 |
| | | | 600/122 |
| 2015/0285685 A1 | 10/2015 | Wax et al. | |
| 2017/0055840 A1 | 3/2017 | Toriyama | |
| 2017/0269095 A1 | 9/2017 | Lee | |
| 2018/0084971 A1* | 3/2018 | Truckai | A61B 1/00082 |
| 2018/0325361 A1* | 11/2018 | Murayama | A61B 1/00096 |
| 2019/0151567 A1* | 5/2019 | Cote | A61M 5/3287 |
| 2020/0005457 A1* | 1/2020 | Ling | A61B 5/0053 |

* cited by examiner

RBC —       — Endothelium

Lumen

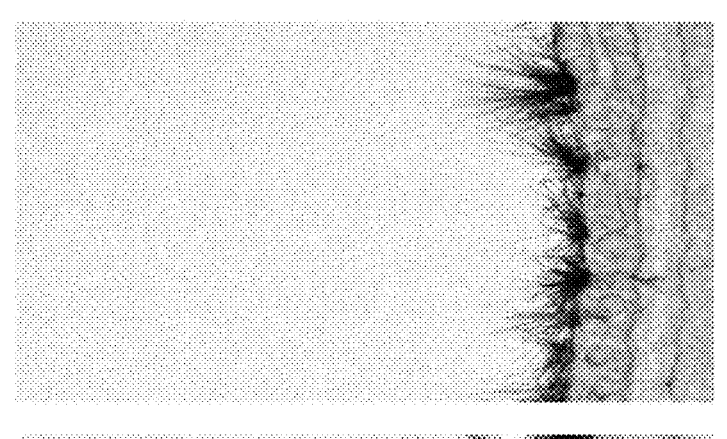
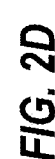
*FIG. 2D*
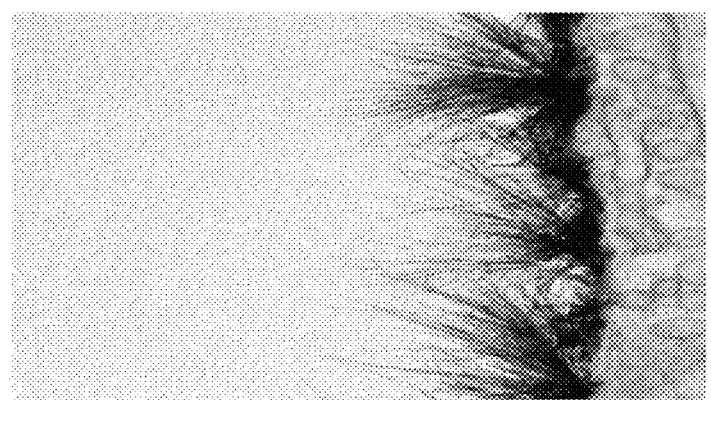
*FIG. 2C*
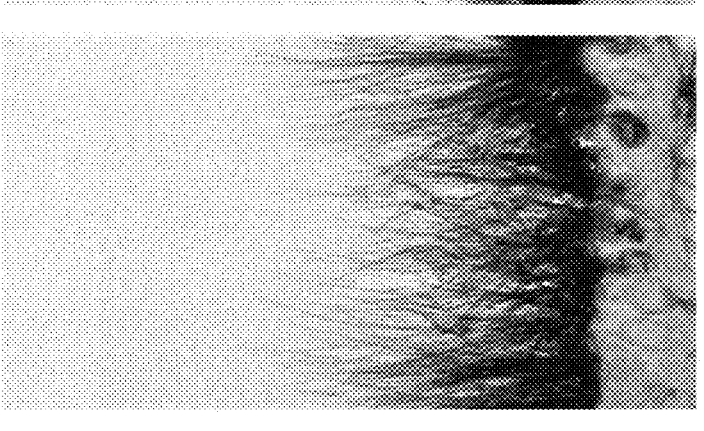
*FIG. 2B*
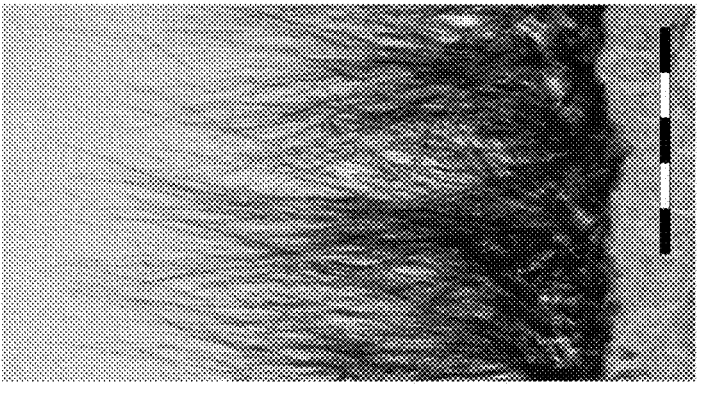
*FIG. 2A*

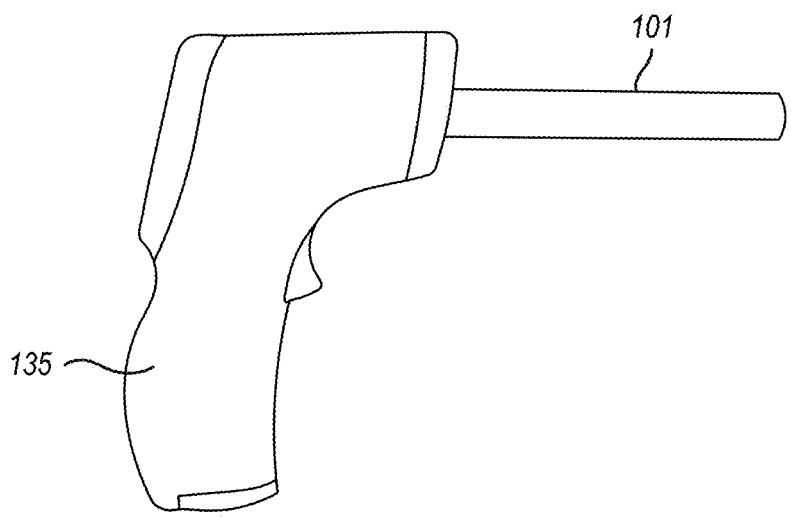
FIG. 8
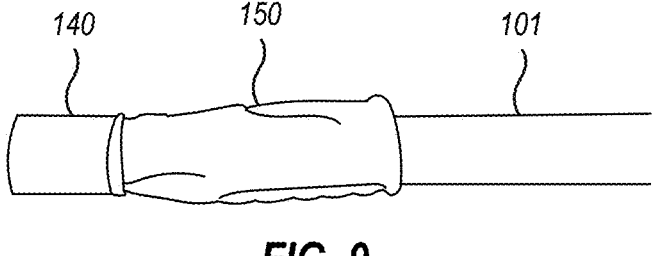
FIG. 9
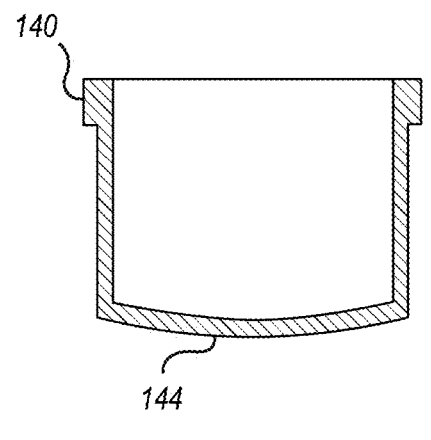
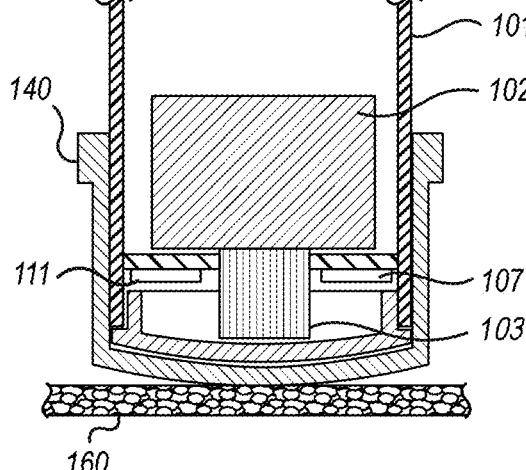
FIG. 10A                    FIG. 10B

METHOD AND APPARATUS FOR MICROVASCULAR VESSEL IMAGING

CROSS-REFERENCE TO RELATED APPLICATIONS

This application claims the benefit of and priority to U.S. Provisional Patent Application Ser. No. 63/143,799 filed on 30 Jan. 2021, and to U.S. Provisional Patent Application Ser. No. 63/222,032 filed on 15 Jul. 2021. Each of the foregoing applications is incorporated in its entirety by reference.

BACKGROUND

Technical Field

This disclosure relates to method and apparatuses for imaging and diagnosing the microvasculature, including imaging and diagnosing the microvascular glycocalyx and conditions thereof.

Related Technology

Study of the vascular system, and circulation through the (micro) vasculature, has contributed to a more fundamental understanding of various physiological mechanisms in the human (and other mammalian) body and has led to the development of more effective clinical diagnostic and therapeutic methods and instruments. Imaging the microvasculature of the vascular system, for example the glycocalyx, is an important method for studying microcirculation. Understanding the static and dynamic nature of microvascular networks such as the glycocalyx and tissue structures of areas under a body's surface is important for many biomedical, academic or clinical applications. Imaging the microvascular of the vascular system is an important method for studying microcirculation.

Microscopic imaging devices have been developed to study and acquire images of these subsurface areas of interest. Computational algorithms have been developed to process and analyze acquired images and to extract useful information for medical professionals and researchers. Existing imaging methods include dark stream imaging and orthogonal polarization imaging. However, these devices and methods are relatively expensive and have only been used in a limited number of research settings. The high cost of these devices prevents academic progress from being applied in conventional medical practices where they can more effectively benefit the population. Additionally, these devices are typically used across multiple patients, presenting a risk of cross-infection from one patient to another. An additional drawback of current imaging devices is a decline in image quality over time, as the device is exposed to physical and/or chemical damage during an imaging process.

The glycocalyx is a polysaccharide-rich layer found on the luminal surface of epithelial cells lining mammalian organs and tissues. In the case of the vascular system, the glycocalyx coats the luminal surface of the endothelium— the vascular endothelial cells lining the inside of all blood vessels. As depicted in FIG. 1, for example, in vivo imaging of a capillary blood vessel illustrates that red blood cells (RBC) flowing through the lumen of the blood vessel do not contact the endothelium of the vessel wall. FIG. 2 is a detailed view of an electron micrograph image capturing a cross-section of a capillary. As depicted, the dense glycocalyx extends from the endothelial cells into the lumen of the blood vessel, forming a micro-thin, gel-like layer.

Until recently, the role of the endothelial glycocalyx had not been well understood. In theory, however, the glycocalyx may act as a protective barrier for the vascular wall or may provide a micro-environment for certain vascular processes. Molecules that associate with the glycocalyx may dynamically interact with the endothelial cells to play a role in orchestrating a variety of functions in the circulatory system. The circulatory system, in turn, plays a role in regulating adequate organ perfusion and in the distribution and exchange of oxygen, nutrients, and hormones within tissues. Furthermore, microcirculation controls tissue hydration and organizes the defense against pathogens.

As illustrated in FIGS. 2A-2D, endothelial glycocalyx can be observed in varying degrees of thickness and/or density, which are indications of the "health" of the endothelial glycocalyx. FIG. 2A, for example, depicts an electron micrograph image of a "healthy" endothelial glycocalyx, while FIG. 2D depicts a severely damaged or perturbed "unhealthy" endothelial glycocalyx. FIG. 2B and FIG. 2C illustrate, respectively, intermediate states of endothelial glycocalyx health (e.g., as indicated visually by the thickness and/or density thereof). The cause(s) of such structural damage and/or depletion of the endothelial glycocalyx remain largely unknown.

Impairment of the glycocalyx barrier through structural damage, depletion, functional deficiency, or other mechanism may be a contributing cause of microvascular endothelial dysfunction, including inflammatory and coagulatory endothelial activation, vascular leakage of fluid, proteins, and other substances (e.g., cholesterol), failure to properly modulate perfused blood vessel density, and other deleterious conditions, leading to general and specific negative vascular health indicators. As depicted in FIG. 3B, for example, an unhealthy endothelial glycocalyx is associated with a "leaky" endothelium, as evidenced by (1) the presence (or "leakage") of cholesterol (or other substances, such as fluids, proteins, etc.) in (or into) the subendothelial space, and (2) a constricted lumen, which may reduce blood flow or perfusion into distal capillaries, muscles, organs, etc., increase blood pressure, and so forth. As illustrated in FIG. 3A, however, a healthy (thick and/or dense) endothelial glycocalyx is associated with a well-formed endothelium and healthy blood vessel structural configuration.

Accordingly, there is a need for devices and processes capable of imaging the endothelial glycocalyx. Such devices and methods should be relatively low cost and capable of use in standard patient settings as opposed to being limited to research institutes.

SUMMARY

A major challenge in the assessment of coronary microvascular dysfunction and its role in the occurrence of myocardial ischemia in microvascular angina (MVA) is that the direct evaluation of the structure and function of small coronary vessels is cumbersome. Conventional imaging devices are bulky and incapable of navigating the small vessels while also providing high resolution images. Embodiments of new methods and devices for microvascular system imaging are disclosed herein that solve some of the problems recognized in the prior art. In some embodiments, an apparatus for imaging the microvascular system and microvascular system comprises an imaging probe including at least one high-resolution image sensor, at least one lens set, one or more optical filters, at least one illumination source, and a housing. In some embodiments, the imaging probe further includes a removable cap. In some embodiments, the at least one lens set is a miniature lens set. In some embodiments, the housing is a tube structure. In some embodiments, the tube may be covered with a protective and/or sterile cover.

In some embodiments, the at least one image sensor and the at least one lens set may be mounted inside the tube and close to a distal opening of the tube. The lens set may be covered by a protective transparent flat cover and is configured to directly contact an area of a body (human or mammalian) to be imaged. For example, the tube may be placed in an area of the body where the microvascular vessels are very close to the surface, such as a sublingual or lip position. In some embodiments, the lens set is configured to provide a focal plane ranging from about 0.2 mm to about 5 mm beyond the distal end of the tube. The lens set may form an image on the high-resolution image sensor.

In some embodiments, the illumination source may include one or more LEDs that may be mounted around the distal opening of the tube. A circular or ring-shaped block may be disposed around an inner side of the LEDs (and/or other illumination source) and is configured to block direct light leakage from the LEDs (and/or other illumination source) into the lens set, which could interfere with the imaging results and increase background noise. The presence of a circular or ring-shaped block to prevent light leakage beneficially results in a higher resolution image and a decrease in background noise, while still allowing for appropriate overall illumination of the targeted anatomy.

In some embodiments, the color of the LEDs is white, green, or a combination thereof. Green light may enhance the contrast of the blood or other vessel since bloodstreams strongly absorb in the green band of the light spectrum. In some embodiments, the probe further includes a color imaging sensor. When the color imaging sensor is employed, white LEDs may be used to provide a much wider band of the light spectrum, including red and blue, allowing the imaging sensor to detect other background information for processing. When only a black and white imaging sensor is used, LEDs providing green light are preferred to detect and image blood vessels.

In some embodiments, the illumination source may include a laser (e.g., green) and/or an optical fiber. Laser light may be much brighter than LED light. In some embodiments, a laser diode illuminates an optical fiber bundle which functions as a light guide and delivers light to the tube distal opening. However, potential interference (constructive or destructive) of the laser light could generate speckles (or background noise) on the illuminated area(s). To prevent and/or remove the speckles, a number of polarizing and/or other films, which cause a phase shift of the laser light, may be applied to the tube, therefore eliminating the interference effects and removing the speckles or other background noise.

In some embodiments, a method of microvascular system imaging includes providing an imaging probe, where the imaging probe is configured to directly contact a surface of a microvascular system component to be imaged. For example, the imaging probe may be configured such that the distal end of the tube directly contacts the surface of tissue containing a blood vessel or microvascular component such as a capillary, a microcapillary, an artery, a vein, a lymph node, a lymphatic vessel, or other similar tissue structure. The method may further include contacting the surface of a microvascular system component and imaging the microvascular system component.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 2A-2D are various images of endothelial glycocalyx, showing progressive diminishing health;

FIG. 8 illustrates an embodiment of a disclosed microvascular imaging device;

FIG. 9 illustrates an embodiment of the microvascular imaging probe of FIG. 8, including a removable cap and sleeve;

FIG. 10A illustrates one embodiment of the removable cap and FIG. 10B illustrates an example of the removable cap implemented on an imaging probe of the present disclosure;

DETAILED DESCRIPTION

Disclosed are methods and apparatuses for microvascular system imaging. In some embodiments, an apparatus for microvascular system imaging is an imaging probe including at least one high-resolution image sensor, at least one lens set, one or more optical filters, an illumination source, and a housing. In some embodiments, the imaging probe additionally includes a removeable cap and protective sleeve. In some embodiments, the lens set may be a miniature lens set. In some embodiments, the housing may a tube structure. In some embodiments, the tube may be covered with a protective and/or sterile cover. The cover may be optically non-distorting.

In some embodiments, the imaging components are disposed at an end of the housing or tube closest to an area or surface of the body (human or mammalian) to be imaged. Such location of the imaging components beneficially enables miniaturization of the overall imaging probe resulting in a less expensive and more user-friendly device. Imaging probes which are big and bulky may be difficult for a user to wield when attempting to navigate to an area for imaging. A more user-friendly device will also beneficially result in cleaner and clearer images due to less movement of the imaging components during imaging. Miniaturizing the device also beneficially enables imaging of much smaller vasculature components than conventional cameras are capable of imaging.

The removable cap may be configured to fit over, or receive, a distal end of the tube. Beneficially, the removeable cap may be disposable, providing protection for patients or other users from cross-infection during an imaging process using an imaging probe of the present disclosure. In some embodiments, the cap is made from an environmentally friendly material. Additionally, the removable cap protects imaging components (exposed or otherwise) of the imaging probe from physical and/or chemical damage. Also beneficially, the removable cap keeps exposed imaging components clean, providing a better- or higher-quality image.

In some embodiments, the removable cap may be part of an illumination light guide included in the imaging probe. In some embodiments, the removable cap may be used as a calibration tool for calibrating the imaging probe. In some embodiments, the removable cap may beneficially prevent unauthorized, unqualified and/or misuse of the imaging probe. For example, the removable cap may prevent misuse of the imaging probe when no cap is used during an imaging process.

Figure 1A:
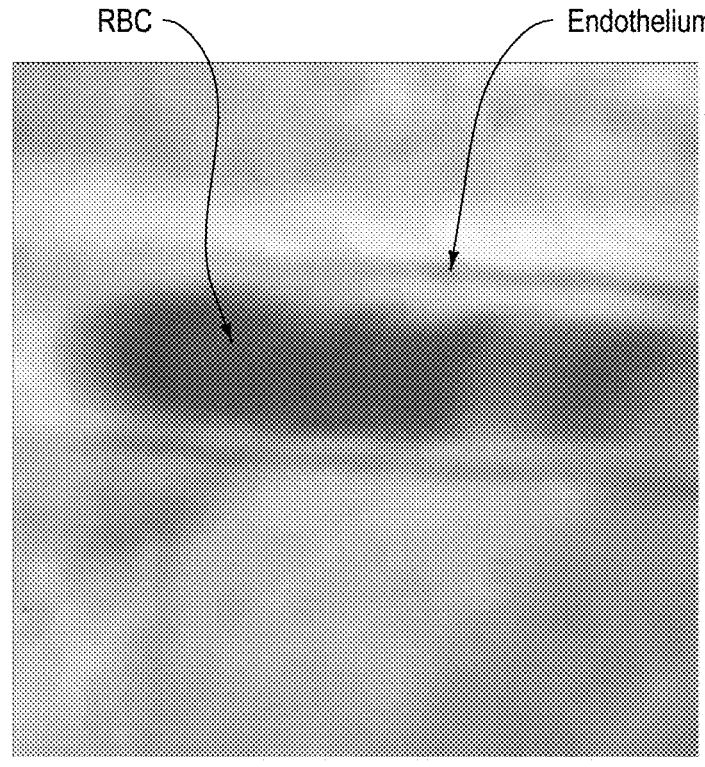
FIG. 1A is an in vivo image of a capillary blood vessel.
Figure 1B:
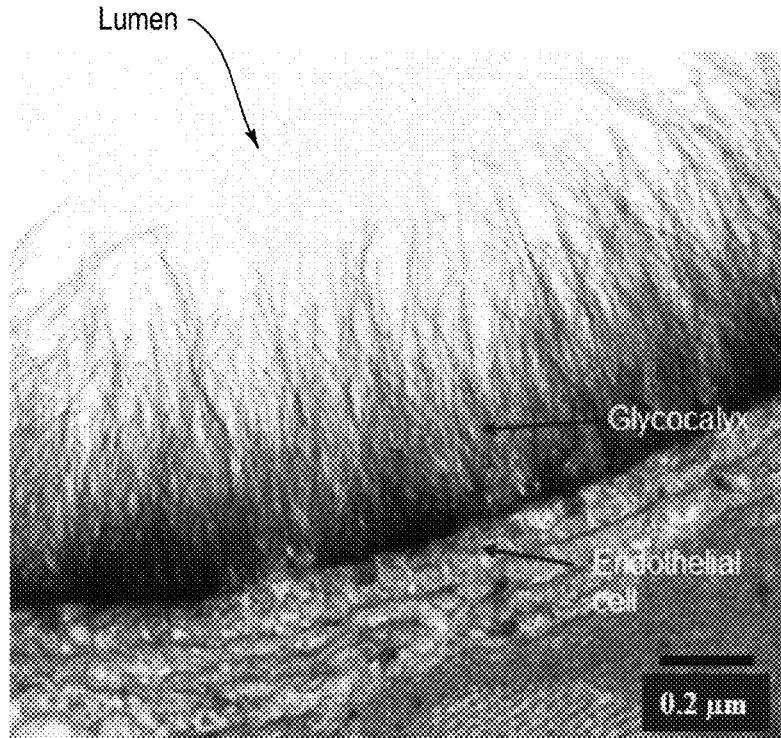
FIG. 1B is a detailed view of an electron micrograph image capturing a cross-section of a capillary blood vessel.
Figure 3A:
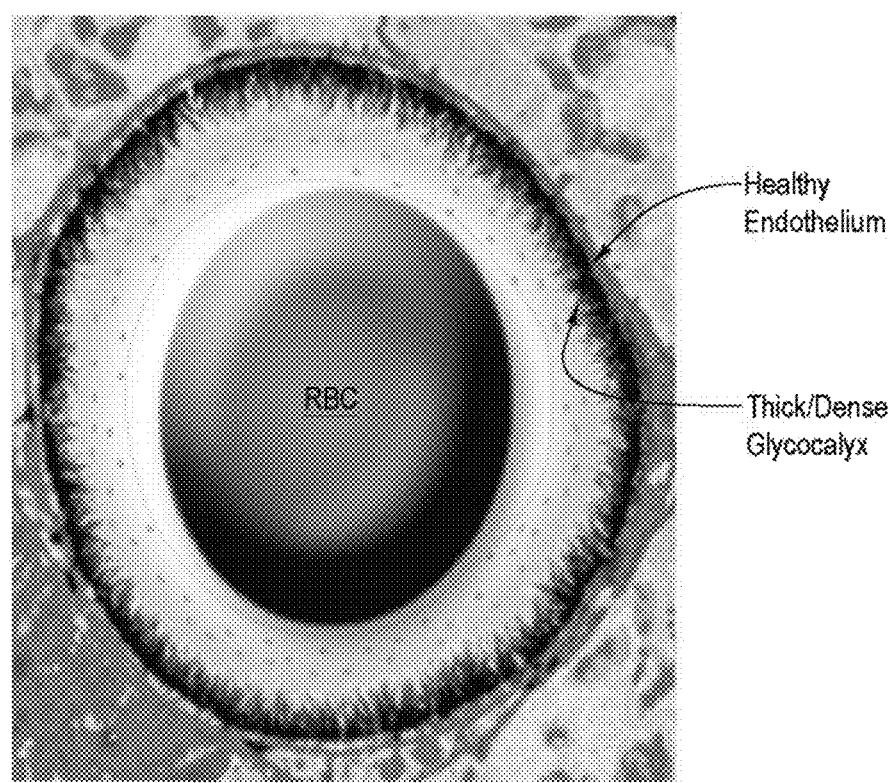
FIGS. 3A illustrates an electron micrograph image capturing a cross-section of a blood vessel having a generally healthy glycocalyx.
Figure 3B:
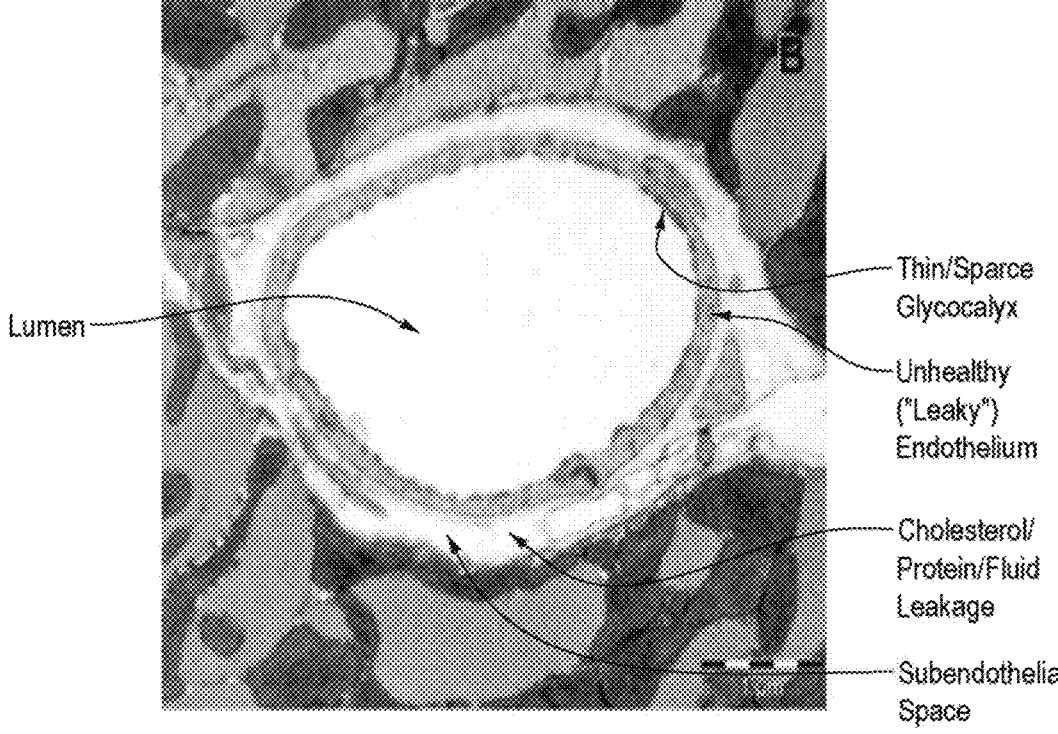
FIGS. 3B illustrates an electron micrograph image capturing a cross-section of a blood vessel having a generally unhealthy glycocalyx.
Figure 4:
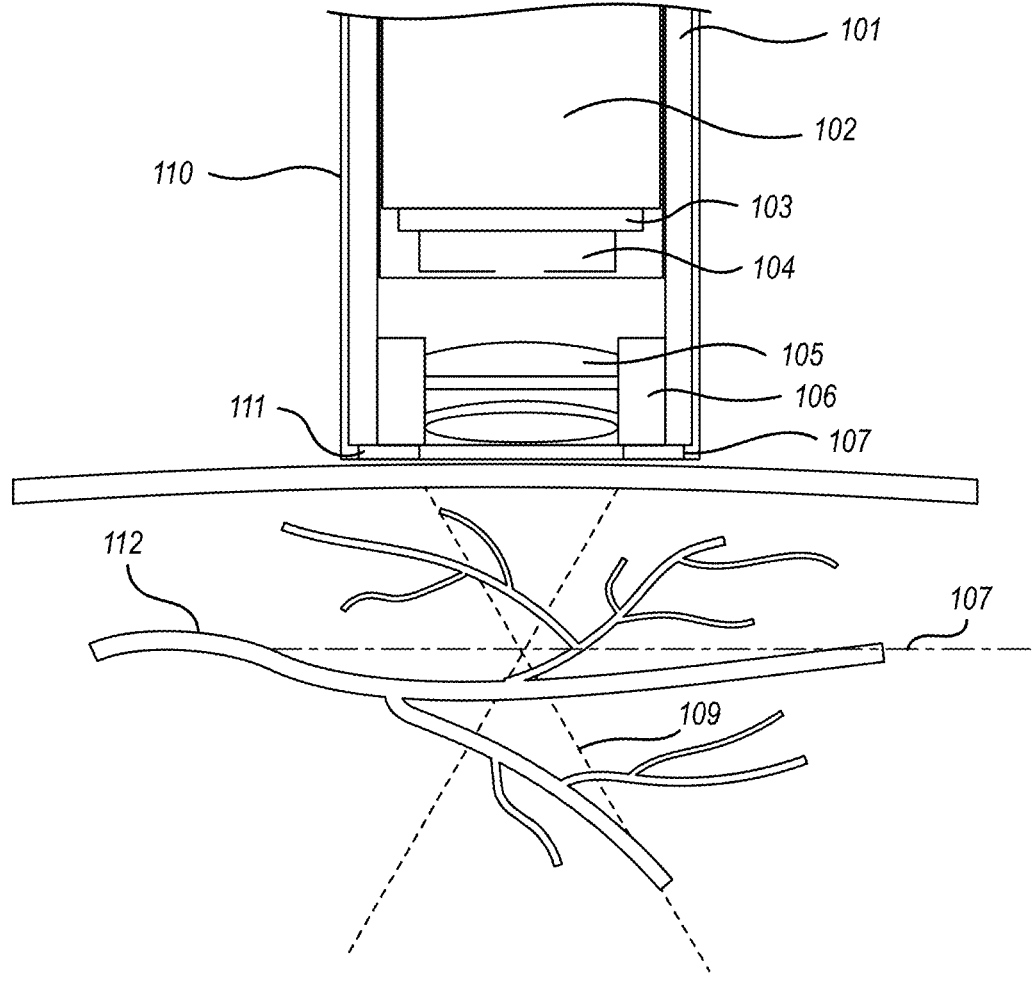
FIG. 4 illustrates one embodiment of a microvascular imaging probe according to the present disclosure.

FIG. 4 illustrates one embodiment of a microvascular imaging probe according to the present disclosure. As illustrated, the imaging probe includes a probe tube 101, a camera control 102, an image sensor 103, an image sensor housing and aperture assembly 104 (which can function to control the amount of light passing to the image sensor 103, a lens set 105 and a lens set holder 106 (also referred to herein as a "circular or ring-shaped block"). The lens set 105 is shown here in relatively large size for ease of viewing, though it will be understood that other implementations of the device utilize a lens set that is smaller relative to the other components. The lens set holder 106 is shown here as terminating slightly proximal of the distal end of the probe tube 101. In other embodiments, the lens set holder 106 extends at least as far as the illumination sources 107, 111. In some embodiments, the lens set holder 106 extends to the distal end of the probe tube 101, such as in contact with the inner surface of probe cover 110. The imaging probe illustrated in FIG. 4 has two illumination sources 107, 111, though only one or more than two illumination sources may be included. Also illustrated in FIG. 4 is an adjustable probe focal plane 108, a ray trace 109 and a microcirculation vessel 112 being imaged by the imaging probe.

In some embodiments, the probe tube 101, optionally covered by the probe cover 110, is configured to internally house the camera control 102, the image sensor 103, image sensor housing and aperture assembly 104, the lens set holder 106, the lens set 105, and one or more illumination sources 107, 111. The probe tube 101 may be any appropriate size for desired microvasculature imaging applications. In some embodiments, the outer diameter of the probe tube may be as small as about 15 mm. other embodiments may have smaller or larger sizes. The minimum size is limited only by the need to fit the imaging components within the probe tube 101, and may change over time as imaging technology advances. The camera control board 102 may be any appropriate printed circuit board (PCB) or any appropriate programmable logic controller (PLC). Though not illustrated, in some embodiments the imaging tube 101 further houses a wireless communication module for wirelessly communicating with a computer system and/or network. The wireless module may be configured to transmit images and/or image data to a central computer or processing network and/or to receive instructions therefrom.

In some embodiments, the image sensor 103 and the lens set 105 may be mounted inside the tube 101 and close to the distal opening of the tube. For example, the image sensor 103 and the lens set 105 may be mounted at the distal most 10 cm of the tube 101, or the distal most 8 cm of the tube, or the distal most 6 cm of the tube, or the distal most 5 cm of the tube, or the distal most 4 cm of the tube, or the distal most 3 cm of the tube, or the distal most 2 cm of the tube, or the distal 1 cm, or a distance within a range with endpoints defined by any two of the foregoing values. Positioning imaging components such as the image sensor 103 and lens set 105 at or near the distal end of the probe tube 101 provides several benefits. For example, placing the imaging components closer to the targeted anatomy to be imaged beneficially minimizes the object-to-image distance between the image sensor 103 and the target. This minimizes the amount of unwanted reflections, debris, or other disruptions that can negatively affect the resulting image data. The shorter distance between the imaging components and the distal end of the probe tube 101 also minimizes the space where dust and other debris can gather and require cleaning and maintenance.

The lens set 105 may be covered by a protective transparent flat cover and is configured to directly contact an area of the human body to be imaged. In some embodiments, such a cover is the same as the cover 110 described elsewhere herein, though in other embodiments, the protective transparent flat cover is included in addition to the cover 110. In some embodiments, such a cover is integrated into the removable cap described elsewhere herein, though in other embodiments, the protective transparent flat cover is included in addition to the removable cap. The protective transparent flat cover may be configured to keep the lens set 105 clean of fluids and/or debris during an imaging process. Further, the protective transparent flat cover is configured to enable the lens set 105 to capture high resolution images. The protective transparent flat cover is optically non-distortive. For example, the tube 101 may be placed in an area of a human body where the microvascular vessels are very close to the surface, such as a sublingual or lip position. In some embodiments, the lens set 105 may provide a focal plane ranging from 0.2 mm to 5 mm beyond the distal end of the tube. The lens set 105 may form an image on the high-resolution image sensor 103. The lens set 105 may be configured to form an image on the high-resolution image sensor 103 in real time.

Figures 6A, 6B:
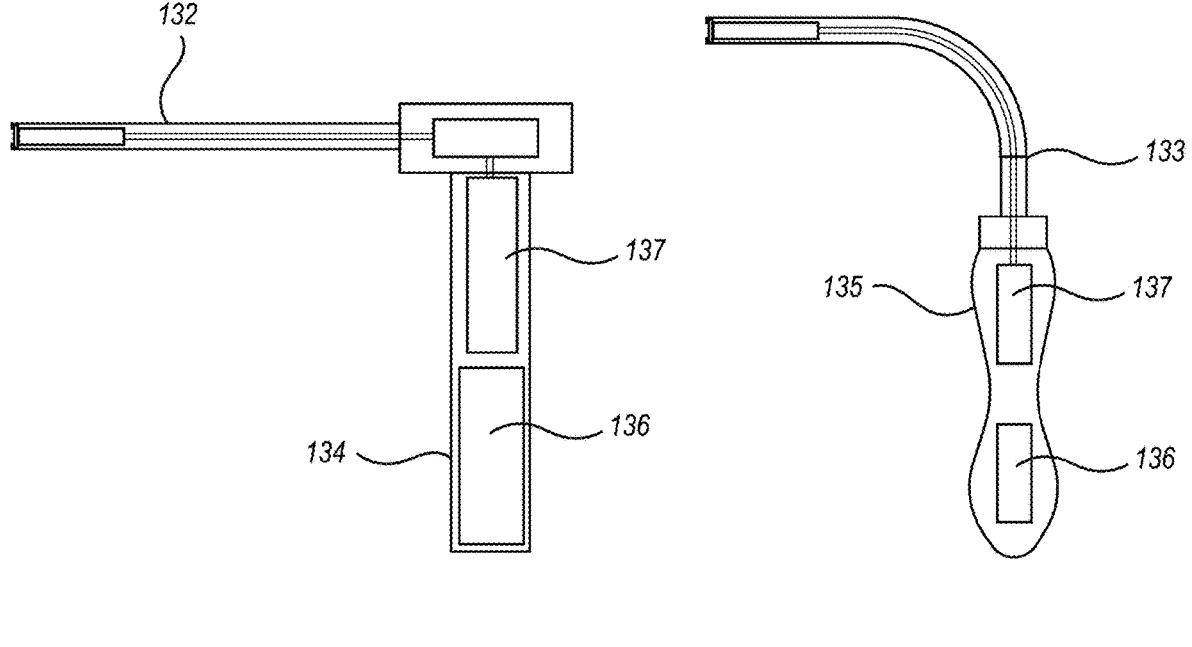
FIGS. 6A-6B illustrate additional embodiments of a microvascular imaging probe according to the present disclosure.

The probe tube 101 may be a rigid tube, or a bendable tube, and may be connected to a probe body (see, for example, FIGS. 6A-B). The probe tube 101 may be a rigid metal or plastic material; additionally, or alternatively, the probe tube 101 may be a bendable plastic or metal material. The probe tube 101 may be constructed from a biologically appropriate material, such as stainless steel or other biocompatible material. The probe tube 101 may include all necessary imaging components for imaging a microvascular vessel in the body (human or other mammalian). A rechargeable and replaceable battery may be embedded in the probe body and/or probe tube 101 to provide the necessary power for imaging and illumination. For example, the battery may provide power to the imaging sensor 103, the lens set 105, and the one or more illumination sources 107, 111.

Figure 5:
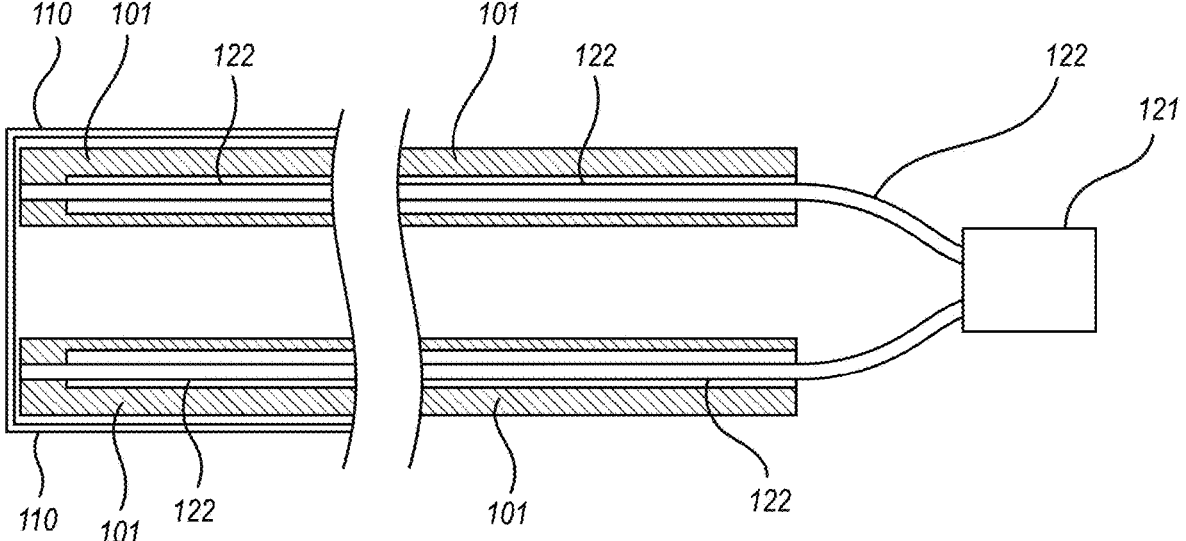
FIG. 5 illustrates one embodiment of a microvascular imaging probe according to the present disclosure utilizing a laser and optical fiber as an illumination source.

FIG. 5 illustrates one embodiment of an imaging probe including a laser and optical fiber as an illumination source. As illustrated, the laser and optical fiber is disposed inside the probe tube 101 of the imaging probe illustrated in FIG. 4, and the features described above in relation to FIG. 4 are applicable to the embodiment of FIG. 5 as well. A laser source 121 may be disposed at or near a proximal end of the probe tube 101 and may be in communication (e.g., optical and electrical) with at least one optic fiber 122. As illustrated in FIG. 5, there are two optic fibers 122. The laser source 121 may be a green, white, or other suitable color/wavelength laser source.

FIGS. 6A-6B illustrates additional and/or alternative embodiments of a microvascular imaging probe according to the present disclosure, and the features illustrated and described in relation to the embodiments of FIGS. 6A-6B may be utilized in conjunction with the features of the embodiments of FIGS. 4 and/or 5. The probe tube 132, 133 may be a rigid tube, or a bendable tube, and may be connected to a probe body 134, 135. At a distal end, the probe tube 132, 133 may include all necessary imaging components for imaging a microvascular vessel in the human body. In some embodiments, the probe tube 132, 133 includes an electronics board 137. In some embodiments, one or more connection wires connects the electronics board 137 to one or more imaging components at or near the distal end of the probe tube 132, 133. In some embodiments, the electronics control board 137 includes a wireless module and a network communication module.

One or more connection wires may send image signals to the electronics board 137 within the probe body 134, 135 and power supply. A rechargeable and replaceable battery 136 may be embedded in the probe body 134, 135 and provide necessary power for imaging and illuminating a microvascular vessel.

Vascular health, particularly health of the endothelial glycocalyx, can be assessed via suitable detection of the endothelial glycocalyx. Methods of such detection and suitable biosensor devices are described in U.S. Pat. No. 8,759,095, the entirety of which is incorporated by reference herein. One suitable method of detection includes the use of the GLYCOCHECK® Microvascular Health Monitor available from MicroVascular Health Solutions, which is a complete imaging solution for screening a subject's or patient's perfused boundary region ("PBR") by accurately measuring and monitoring changes in the PBR in real time. The PBR in microvessels is the cell-poor layer which results from phase separation between the flowing red blood cells ("RBC") and plasma and represents the most luminal part of the endothelial glycocalyx that allows cell penetration. Loss of endothelial glycocalyx integrity allows for deeper penetration by the outer edge of the RBC-perfused lumen, thereby increasing PBR, resulting in increased vulnerability of the endothelium.

PBR is thus a measure for the depth of penetration of red blood cells in the glycocalyx (or into the region where healthy glycocalyx should be found). Low values of PBR indicate a mechanically stable glycocalyx that protects the vessel wall against damage by circulating blood cells and other constituents, molecules or reagents circulating in the blood. The PBR is the main readout parameter calculated by the GLYCOCHECK® software. Calculation of further qualitative and/or quantitative (e.g., scores or numeric) measurements or representations can be performed manually or automatically (e.g., by the GLYCOCHECK® software).

The measurement may be performed non-invasively with a disclosed imaging probe being placed under the patient's tongue, under-arm area, vagina, rectum, or other (highly) vascular area. It is noted that such measurements, while providing a local read of blood vessel structural features is highly indicative of an overall and/or systemic vascular landscape. For instance, measurements taken from one of the aforementioned locations can be confirmed (as accurate and representative of systemic vascular landscape) by measurement at other locations.

Other measurable indicators include (blood) volume, width and dimension of the glycocalyx, vessel density, the number of perfused vessels per tissue surface versus total number of vessels, RBC filling percentage, capillary volume reserve, and presence or absence of glycocalyx contributing constituents, etc. Changes in any of the foregoing parameters, alone or in combination, are useful indicators for assessing vascular health.

Figure 7:
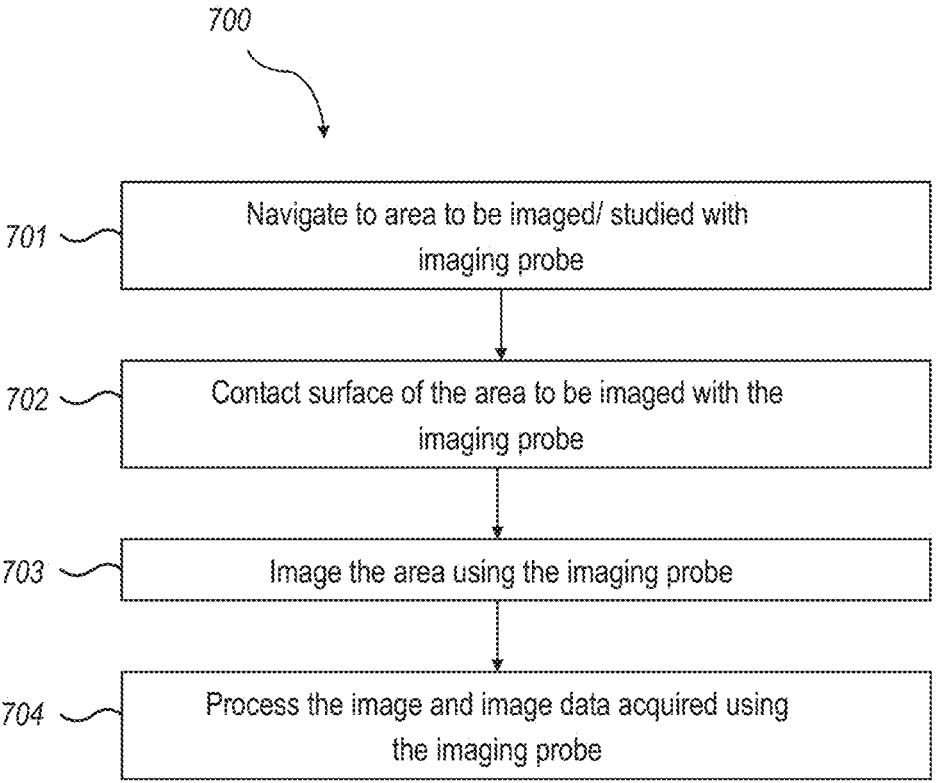
FIG. 7 is a flowchart of an example method according to the present disclosure.

FIG. 7 illustrates one embodiment of a disclosed method of imaging a microvascular system component. In some embodiments, a method of microvascular system imaging includes providing an imaging probe, where the imaging probe is configured to directly contact a surface of a microvascular system component. For example, the imaging probe may be configured to directly contact the surface of a blood vessel such as a capillary, an artery, or a vein, or a lymph node, lymphatic vessel, or other similar component, or to tissue containing one or more of the foregoing. The method may also include navigating the imaging probe to an area to be imaged or studied in the body (human or mammalian) (step 701). The method may further include contacting the surface of the area to be imaged, where the area includes a microvascular system component, and imaging the microvascular system component (steps 702 and 703).

Imaging the microvascular system component may include adjusting the focal plane of the imaging probe. In some embodiments, the lens set of the imaging probe may have a focal plane ranging from 0.2 mm to 5 mm beyond the distal end of the tube. In some embodiments, images of the microvascular system component are acquired at a depth of 0.2 mm, 0.3 mm, 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm or at a depth within a range with endpoints defined by any two of the foregoing values.

In some embodiments, adjustment of the focal plane occurs by pressing a control button, moving a control wheel, or actuating some other manual control disposed on an exterior of the imaging tube. Adjustment may additionally or alternatively occur automatically through an auto-focus mechanism embedded in, for example, the image sensor or the lens set. In some embodiments, a computer system may implement an auto-focus algorithm to adjust the focal plane.

In some embodiments, the method further includes processing the acquired images and image data from the imaging probe (step 704). In some embodiments, the images and image data may be displayed to an operator. In some embodiments, the images and imaging data are sent to a central processor via direct wired connection and/or a wireless connection, such as Wi-Fi and/or Bluetooth.

Imaging the microvascular system component beneficially enables a physician or other medical practitioner to identify and diagnose conditions of, or relating to, the glycocalyx. Imaging microvascular system components using the disclosed imaging probe beneficially provides high-resolution images, where such images may be in color, black and white, or both.

FIG. 8 illustrates another embodiment of a microvascular imaging probe according to the present disclosure, and the features illustrated and described in relation to the embodiments of FIG. 8 may be utilized in conjunction with the features of the embodiments of FIGS. 4-6B. As illustrated, the microvascular imaging probe includes a probe body 135 and an imaging tube 101.

Figure 12:
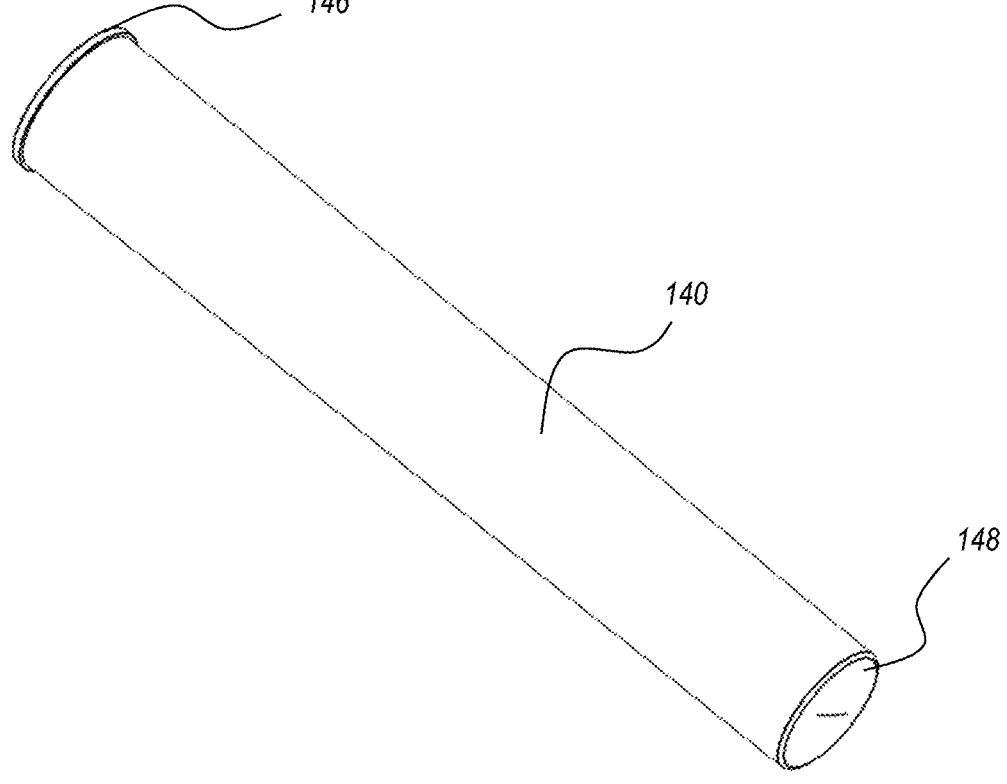
FIG. 12 illustrates another embodiment of a removable/disposable cap.

FIG. 9 illustrates an embodiment of the microvascular imaging probe of FIG. 8 including a removable cap 140 and a sleeve 150. The removable cap 140 may, in some embodiments, correspond to the tube cover 110 discussed above. As illustrated, the sleeve 150 covers a portion of the imaging tube 101, and the removable cap 140 is placed at a distal end of the imaging tube 101 over the sleeve 150. In the illustrated embodiment, the removable cap 140 is disposed over a short length of the distal end of the imaging tube 101. In other embodiments, such as shown in FIG. 12, the cap 140 is longer, and may be sized to cover substantially all of the probe tube 101. In some embodiments, when used, the sleeve 150 maintains sterility of the imaging tube. The sleeve 150 in combination with the removable cap 140 enables protection of the imaging tube 101 and contained imaging components from bodily fluids and microbes. Alternatively, when the cap 140 covers substantially all of the outer surface of the probe tube 101, the cap 140 functions to protect the probe tube 101 and associated imaging components.

The removable cap 140 may be made from a rigid metal and the sleeve 150 is made from a flexible, elastic material. In some embodiments, the removable cap 140 may be made from a rigid plastic material. In some embodiments, the sleeve 150 is made from an elastic material, such as rubber, silicone, nitrile, latex, vinyl, or a combination of elastic materials. In some embodiments, the removable cap 140 is coupled to the sleeve 150 via glue, elastic pressure or a friction fit, for example. In some embodiments, the sleeve 150 is a thin membrane sleeve made from a polymer and/or polymer composite material. In some embodiments, the removable cap 140 and/or the sleeve 150 may be sterilized prior to use with an imaging probe in an imaging process. For example, the removable cap 140 and/or the sleeve 150 may be sterilized via radiation.

FIG. 10A illustrates one embodiment of the removable cap and FIG. 10B illustrates an example of the removable cap implemented on an imaging probe of the present disclosure. The features illustrated and described in relation to the embodiments of FIG. 10A-10B may be utilized in conjunction with the features of the embodiments of FIGS. 4-6B and 8-9. As illustrated in FIG. 10A, the removable cap 140 is sealed at one end 144 and is open at the other, opposing end. In some embodiments, the removable cap 140 may be configured to fit over an imaging tube at the open, distal end of the removable cap 140. In some embodiments, the sealed end 144 of the removable cap is transparent and configured to allow light to pass through. In this manner, the cap 140 is intended to remain on the probe tube 101 during an imaging procedure.

In some embodiments, the sealed end 144 of the removable cap is curved or a non-flat shape or has curvature. When an imaging probe containing the removable cap is placed in contact with the location to be imaged (i.e., the surface of the area of the body to be imaged or the target anatomy), the curvature of the sealed end 144 of the cap 140 may be configured to expel potential or present bubbles which hinder image quality. For example, when imaging a sublingual location that may be covered by saliva, the curvature of the sealed end 144 of the cap 140 may enable acquisition of images with a clearer image quality (i.e., higher resolution) by expulsion of bubbles present at the surface of the area to be imaged.

FIG. 10B illustrates the removable cap of FIG. 10A implemented on an imaging probe tube 101 of an imaging probe. The illustrated imaging probe tube 101 may internally house a camera control 102, an image sensor 103, and one or more illumination sources 107, 11. The camera control 102, image sensor 103, and one or more illumination sources 107, 11 may be mounted at a distal end of the imaging probe tube 101. The removable cap 140 may be configured to fit over the distal end of the imaging probe tube 101 where the imaging components (e.g., camera control 102, image sensor 103, etc.) are mounted or contained.

The removable cap 140 may be mounted or connected to the distal end of the imaging tube 101 by friction fit, mechanical fit, a removable adhesive, detent, screwed fittings, or any combination. For example, the removable cap 140 may be mounted and held in place at the distal end of the imaging tube 101 through pressure between an interior wall of the cap 140 and an exterior surface of the imaging tube 101. Additionally, or alternatively, the removable cap 140 may be mounted and held in place at the distal end of the imaging tube 101 through pressure between the interior wall of the cap 140 and the sleeve illustrated in FIG. 9. In some embodiments, the removable cap 140 may be secured to the distal end of the imaging tube 101 using a rotating coupling mechanism.

The sealed end 144 of the removable cap 140 is exposed and configured to contact a surface of an area of a body, or target anatomy, to be imaged. As illustrated in FIG. 10B, the sealed end 144 of the removable cap 140 is contacting a surface of skin 160, where the surface of the skin 160 is the anatomy to be imaged. The sealed end 144 of the removable cap 140 may be transparent and configured to allow light to pass through. In some embodiments, the sealed end 144 is transparent and configured to allow more than 50% transmission of light, such as 60%, 65%, 75%, 80%, 100% transmission of light, or within a range with endpoints defined by any two of the foregoing values. In some embodiments, the sealed end 144 is transparent and configured to allow up to 50%, such as 30%, 35%, 40%, 45% transmission of light or within a range with endpoints defined by any two of the foregoing values. In some embodiments, the sealed end 144 of the removable cap 140 may be curved or flat. In some embodiments, the removable cap 140 may function as the first optical imaging and illumination component of an overall imaging system.

Figures 11A, 11B, 11C:
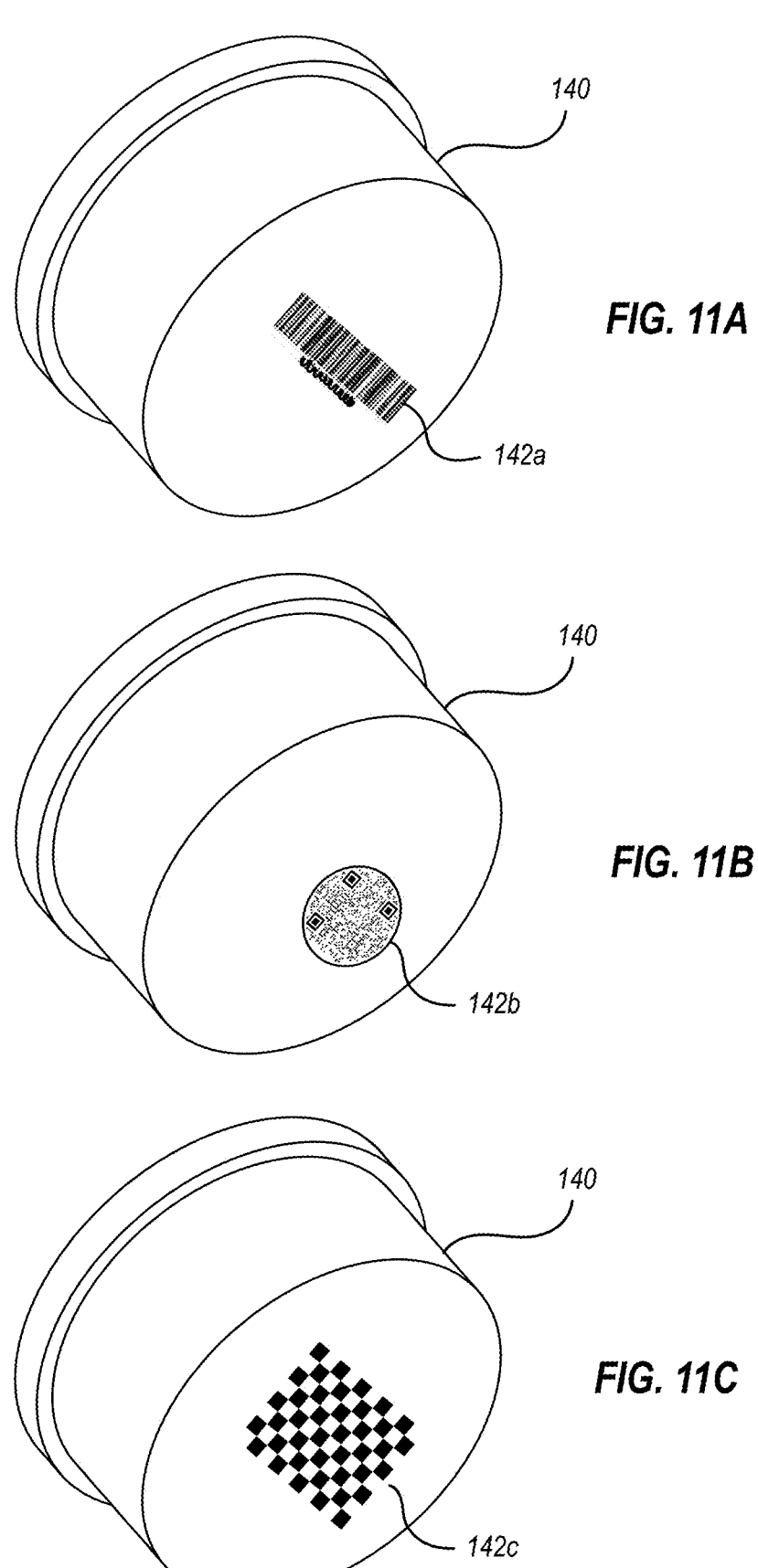
FIGS. 11A-11C illustrate embodiments of the removable cap with various barcodes and/or patterns.

FIGS. 11A-11C illustrate embodiments of the removable cap 140 with various barcodes and/or patterns. The features illustrated and described in relation to the embodiments of FIG. 11A-11C may be utilized in conjunction with the features of the embodiments of FIGS. 4-6B and 8-10B. In some embodiments, the sealed and transparent end of the removable cap 140 may contain a scannable symbol or pattern, such as 1D (FIG. 11A) or 2D (FIG. 11B) barcodes 142_a_, 142_b_ (shown here in exaggerated form). In some embodiments, imaging software is enabled to identify whether a removable cap 140 is authorized or qualified and, similarly, unauthorized or unqualified, for a particular imaging process. For example, upon startup of the device and/or upon initiation of a procedure, the camera control can operate to scan the removable cap 140 for a code. The data embedded in the code can then be transmitted to a network where it is determined whether the particular cap associated with the code has been used previously (e.g., which would disqualify it for potentially detrimental reuse) and/or is otherwise authorized for use. If the code is not found and/or returns a disqualification message, the software can function to prevent further imaging using the device.

In some embodiments, the sealed and transparent end of the removable cap 140 may contain micro-calibration patterns 142c, such as that illustrated in FIG. 11C. In some embodiments, the micro-calibration patterns 142c are configured to be read by imaging software. In some embodiments, imaging software is configured to read a micro-calibration pattern 142c disposed on the sealed and transparent end of the removable cap 140 to correct optical distortion of the imaging probe, to perform an initial focal plane calibration, and/or to provide other calibration checks.

In some embodiments, the sealed and transparent end of the removable cap 140 may be coated with a coating. In some embodiments, the coating is a hard coating. In some embodiments, the coating is an anti-reflection coating. In some embodiments, the coating is a light-filtering coating or film, such as a polarizing coating or film. In some embodiments, the coating is a combination of hard, anti-reflection, light-filtering and/or polarizing coatings. In some embodiments, the sealed end of the removable cap 140 is a polarizer.

FIG. 12 illustrates another configuration of the removable cap 140 with a length that substantially matches the length of the probe tube 101. The illustrated removable cap 140 extends between an open proximal end 146 and a sealed distal end 148. The removable cap features discussed above are also applicable to the removable cap of FIG. 12. The removable cap 140 may include a variably sized inner diameter such that the distal section fits tighter around the probe tube 101 to provide a friction fit. Additionally, or alternatively, the removable cap 140 may include a rotation lock, a spring-based (i.e., "click") lock, a snap fitting, threaded portions that engage with matching threads of the probe tube, and/or other attachment means described herein or otherwise known in the art.

In some embodiments, the removable cap 140 is manufactured to prevent unauthorized use (such as improper reuse), by including features that render the cap unusable if a user attempts to sterilize the cap. For example, the removable cap 140 may include an additive that reacts with alcohol to become more opaque, thereby rendering the cap unusable for subsequent imaging. Such additives are known to the person of skill in the art.

Some embodiments of the present disclosure can include systems and/or methods for diagnosing vascular impairment or health in a human or non-human mammalian patient or subject. Some embodiments can include computer systems, hardware storage devices, and/or methods for determining glycocalyx impairment using a dynamically extrapolated characterization of a plurality of microvascular vessels. In particular, a microscopy image of a plurality of microvascular vessels can be captured using a disclosed imaging probe, such as the imaging probe illustrated in FIGS. 6A-B and/or FIGS. 8-10B. Image data corresponding to at least some of the microvascular vessels captured within the microscopy image can be segmented into a plurality of segmented data portions.

A profile can be generated for each of the segmented data portions. The profiles can be compiled together and an extrapolated characterization of the compiled profiles can be created. The extrapolated characterization can be compared against a predetermined threshold value in order to select a target characterization level from within the extrapolated characterization. A particularized set of rules can be applied to the target characterization level to generate a glycocalyx impairment determination. The glycocalyx impairment determination can displayed on a user interface and/or conveyed as a diagnosis to vascular impairment.

Some embodiments can incorporate or include diagnosing a human or non-human mammalian patient or subject as suffering from glycocalyx dysfunction or impairment in response to the generation of a glycocalyx impairment determination. Some embodiments can incorporate or include assessing and/or determining the health, functionality, and/or impairment of the glycocalyx as a function of blood flow, in a human or non-human mammalian patient or subject.

To achieve these and other benefits, embodiments of the imaging probe capture a microscopy image of a plurality of microvascular vessels. Then, image data corresponding to at least some of the microvascular vessels captured within the microscopy image is segmented into a plurality of segmented data portions. Subsequently, a profile is generated for each of these segmented data portions. These profiles are then compiled together. Once the profiles are compiled together, then an extrapolated characterization of the compiled profiles is created. Next, the extrapolated characterization is compared against a predetermined threshold value in order to select a target characterization level from within the extrapolated characterization. Then, a particularized set of rules is applied to the target characterization level to generate a glycocalyx impairment determination. Finally, this glycocalyx impairment determination is displayed on a user interface. Examples of computer systems and softwares suitable for this processing, segmenting and profile generation are described in PCT Application Serial No. PCT/US18/31686 titled "COMPOSITIONS, SYSTEMS, AND METHODS FOR ASSESSING AND IMPROVING VASCULAR HEALTH AND TREATMENTS INVOLVING THE SAME," the contents of which are incorporated in their entirety herein by reference.

Additional Computer System Details

It will be appreciated that in this description and in the claims, the term "computer system", "controller" (such as the camera control 102 and/or electronics board 137), or "computing system" is defined broadly as including any device or system—or combination thereof—that includes at least one physical and tangible processor and a physical and tangible memory capable of having stored thereon computer-executable instructions that may be executed by a processor. By way of example, not limitation, the term "computer system" or "computing system," as used herein is intended to include personal computers, desktop computers, laptop computers, tablets, hand-held devices (e.g., mobile telephones, PDAs, pagers), microprocessor-based or programmable consumer electronics, minicomputers, mainframe computers, multi-processor systems, network PCs, distributed computing systems, datacenters, message processors, routers, and switches.

The memory may take any form and may depend on the nature and form of the computing system. The memory can be physical system memory, which includes volatile memory, non-volatile memory, or some combination of the two. The term "memory" may also be used herein to refer to non-volatile mass storage such as physical storage media, which can also be referred to as hardware storage devices.

The computing system also has thereon multiple structures often referred to as an "executable component." For instance, the memory of computing system can include an executable component for operating the controller and/or functions of the elevation systems and/or circular reciprocation systems disclosed herein. The term "executable component" is the name for a structure that is well understood to one of ordinary skill in the art in the field of computing as being a structure that can be software, hardware, or a combination thereof.

For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. Such a structure may be computer-readable directly by a processor—as is the case if the executable component were binary. Alternatively, the structure may be structured to be interpretable and/or compiled—whether in a single stage or in multiple stages—so as to generate such binary that is directly interpretable by a processor.

The term "executable component" is also well understood by one of ordinary skill as including structures that are implemented exclusively or near-exclusively in hardware logic components, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination thereof The terms "component," "service," "engine," "module," "control," "generator," or the like may also be used in this description. As used in this description and in this case, these terms—whether expressed with or without a modifying clause—are also intended to be synonymous with the term "executable component" and thus also have a structure that is well understood by those of ordinary skill in the art of computing.

While not all computing systems require a user interface, in some embodiments a computing system includes a user interface for use in communicating information from/to a user. For example, a user interface can be used by a user to dictate their desired operation of the modified magnet assembly. The user interface may include output mechanisms as well as input mechanisms (e.g., I/O Devices). The principles described herein are not limited to the precise output mechanisms or input mechanisms as such will depend on the nature of the device. However, output mechanisms might include, for instance, speakers, displays, tactile output, projections, holograms, and so forth. Examples of input mechanisms might include, for instance, microphones, touchscreens, projections, holograms, cameras, keyboards, stylus, mouse, or other pointer input, sensors of any type, and so forth.

Accordingly, embodiments described herein may comprise or utilize a special purpose or general-purpose computing system. Embodiments described herein also include physical and other computer-readable media for carrying or storing computer-executable instructions and/or data struc tures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments disclosed or envisioned herein can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium that can be used to store desired program code in the form of computer-executable instructions or data structures and that can be accessed and executed by a general purpose or special purpose computing system to implement the disclosed functionality of the invention. For example, computer-executable instructions may be embodied on one or more computer-readable storage media to form a computer program product. For the absence of doubt, such computer-readable storage media can also be termed "hardware storage devices," which are physical storage media—not transmission media.

Transmission media can include a network and/or data links that can be used to carry desired program code in the form of computer-executable instructions or data structures and that can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Those skilled in the art will further appreciate that a computing system may also contain communication channels that allow the computing system to communicate with other computing systems over, for example, a network. Accordingly, the methods described herein may be practiced in network computing environments with many types of computing systems and computing system configurations. The disclosed methods may also be practiced in distributed system environments where local and/or remote computing systems, which are linked through a network (either by hardwired data links, wireless data links, or by a combination of hardwired and wireless data links), both perform tasks. In a distributed system environment, the processing, memory, and/or storage capability may be distributed as well.

ADDITIONAL TERMS & DEFINITIONS

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An imaging probe for imaging a microvascular system component, the probe comprising:
an imaging tube with a proximal end and a distal end, wherein the imaging tube internally houses at least one image sensor, at least one lens set, and an illumination source;
a body connected to the proximal end of the imaging tube;
a distal element disposed at the distal end of the imaging tube, the distal element comprising a curved, distal-facing surface with a first radius of curvature; and a removable cap configured to fit over the distal element and over at least a distal portion of the imaging tube,
wherein the removable cap is formed from a rigid material and comprises a cylindrical body and a curved, optically transparent distal-facing surface, wherein the cylindrical body and curved, optically transparent distal-facing surface join to form an edge,
wherein the curved, optically transparent distal-facing surface comprises a second radius of curvature that substantially matches the first radius of curvature.

2. The imaging probe of claim 1, wherein the at least one image sensor is a color charge-coupled device (CCD) sensor, a black and white CCD sensor, a color complementary metal-oxide-semiconductor (CMOS) sensor, or a black and white CMOS sensor.

3. The imaging probe of claim 1, wherein the imaging tube comprises an adjustable focal plane ranging from 0.2 mm to 5 mm beyond the distal end of the imaging tube.

4. The imaging probe of claim 3, wherein the adjustable focal plane is adjusted by one or more of an embedded auto-focus mechanism in the imaging tube or an autofocus algorithm implemented in a separate processing board.

5. The imaging probe of claim 1, wherein the illumination source comprises one or more light emitting diodes (LEDs) mounted at or near the distal end of the imaging tube.

6. The imaging probe of claim 1, wherein the illumination source comprises at least one optical fiber disposed along a wall of the imaging tube and terminating at or near the distal end of the imaging tube.

7. The imaging probe of claim 6, wherein a laser source is connected to the at least one optical fiber.

8. The imaging probe of claim 6, wherein a polarizing film covers a distal terminal end of the at least one optical fiber.

9. The imaging probe of claim 8, wherein the illumination source comprises a plurality of optical fibers.

10. The imaging probe of claim 9, wherein each optical fiber is covered by the polarizing film.

11. The imaging probe of claim 10, wherein a polarization direction of the polarizing film is not aligned across the plurality of optical fibers covered with the polarizing film.

12. The imaging probe of claim 1, wherein the removable cap has a length that substantially matches a length of the imaging tube.

13. The imaging probe of claim 1, wherein the removable cap includes a scannable symbol or pattern configured to enable one or more of use authorization, misuse prevention, or imaging calibration.

14. The imaging probe of claim 1, wherein the removable cap is configured to attach to the probe tube via one or more of a friction fit, a rotation lock, a spring lock, a snap fit, or combinations thereof.

15. A method of imaging a mammalian microvascular system component, the method comprising: contacting a tissue surface with an imaging probe as in claim 1; and imaging the microvascular system component.

* * * * *